United States Patent [19]
Buchanan et al.

[11] Patent Number: 5,976,300
[45] Date of Patent: Nov. 2, 1999

[54] METHOD OF SEALING A PORT TUBE IN A CONTAINER

[75] Inventors: Bradley Buchanan, Ross, Calif.; Larry Rosenbaum, Gurnee; Sidney T. Smith, Lake Forest, both of Ill.

[73] Assignee: Baxter International Inc., Deerfield, Ill.

[21] Appl. No.: 08/990,503

[22] Filed: Dec. 15, 1997

Related U.S. Application Data

[63] Continuation of application No. 08/675,529, Jul. 3, 1996, abandoned.

[51] Int. Cl.[6] .............................. B32B 31/20; F16L 13/02
[52] U.S. Cl. ................................... 156/273.7; 156/274.4; 156/293; 156/308.2; 604/408; 493/189; 493/206; 493/209
[58] Field of Search ..................... 156/196, 212, 156/245, 273.7, 274.4, 275.1, 293, 294, 308.2, 308.4, 309.6; 493/189, 206, 209, 212, 213, 927; 604/408

[56] References Cited

U.S. PATENT DOCUMENTS

| D. 285,725 | 9/1986 | Franchere . |
|---|---|---|
| 2,816,596 | 12/1957 | Welch . |
| 3,078,201 | 2/1963 | Christie . |
| 3,255,923 | 6/1966 | Soto . |
| 3,558,397 | 1/1971 | Clark . |
| 3,570,375 | 3/1971 | Williams et al. . |
| 3,912,843 | 10/1975 | Brazier . |
| 3,995,084 | 11/1976 | Berger et al. . |
| 4,005,710 | 2/1977 | Zeddies et al. . |
| 4,022,256 | 5/1977 | Berkman et al. . |

(List continued on next page.)

FOREIGN PATENT DOCUMENTS

| 63709/90 | 11/1991 | Australia . |
|---|---|---|
| 0 092 897 A2 | 11/1983 | European Pat. Off. . |
| 0 148 161 A2 | 7/1985 | European Pat. Off. . |
| 0 310 143 A1 | 4/1989 | European Pat. Off. . |
| 0 446 505 A1 | 9/1991 | European Pat. Off. . |
| 0 488 544 A1 | 6/1992 | European Pat. Off. . |
| 0 491 380 A2 | 6/1992 | European Pat. Off. . |
| 0 539 800 A2 | 5/1993 | European Pat. Off. . |
| 0 539 800 A3 | 5/1993 | European Pat. Off. . |
| 0 552 412 A1 | 7/1993 | European Pat. Off. . |

(List continued on next page.)

OTHER PUBLICATIONS

Hong, K. Z., Ph.D., *Thermoplastics for Health–Care Products —Clear Choices Are Not So Clear.*

Wigotsky, Victor, *Medical Plastics*, Plastics Engineering, pp. 18–22, Oct. 1995.

*Primary Examiner*—Michael W. Ball
*Assistant Examiner*—Michael A Tolin
*Attorney, Agent, or Firm*—Wallenstein & Wagner, Ltd.

[57] ABSTRACT

The present invention provides a method for connecting rounded members between planar members comprising the steps of providing a rounded member having an outer layer having a first melting temperature range and an inner layer concentrically disposed within the outer layer and having a second melting temperature range, the second melting temperature range being warmer than the first melting temperature range, providing a pair of opposed planar members, the planar members each having a melting temperature within the first melting temperature range, positioning an end portion of the rounded member between perimeter edges of the pair of planar members to define an interface area, applying pressure to the interface area to collapse the end portion of the rounded member to essentially a flattened position, applying sealing energy to the interface area to heat the rounded member to a temperature within the first melting temperature range but below the second melting temperature range, thereby forming a weld between the planar members, and the rounded member in the interface area, and, releasing the pressure to the interface area wherein the end portion of the rounded member returns to an open position.

22 Claims, 4 Drawing Sheets

U.S. PATENT DOCUMENTS

| | | |
|---|---|---|
| 4,023,607 | 5/1977 | Jensen et al. . |
| 4,045,515 | 8/1977 | Isaka et al. . |
| 4,085,244 | 4/1978 | Stillman . |
| 4,103,686 | 8/1978 | LeFevre . |
| 4,112,989 | 9/1978 | Grode et al. . |
| 4,140,162 | 2/1979 | Gajewski et al. . |
| 4,226,822 | 10/1980 | Yoshikawa et al. . |
| 4,227,527 | 10/1980 | De Frank et al. . |
| 4,244,378 | 1/1981 | Brignola . |
| 4,261,473 | 4/1981 | Yamada et al. . |
| 4,286,628 | 9/1981 | Paradis et al. . |
| 4,310,017 | 1/1982 | Raines . |
| 4,322,465 | 3/1982 | Webster . |
| 4,333,968 | 6/1982 | Nahmias . |
| 4,369,812 | 1/1983 | Paradis et al. . |
| 4,405,667 | 9/1983 | Christensen et al. . |
| 4,417,753 | 11/1983 | Bacehowski et al. . |
| 4,421,235 | 12/1983 | Moriya . |
| 4,465,487 | 8/1984 | Nakamura et al. . |
| 4,479,989 | 10/1984 | Mahal . |
| 4,497,857 | 2/1985 | Bonis . |
| 4,521,437 | 6/1985 | Storms . |
| 4,540,537 | 9/1985 | Kamp . |
| 4,546,085 | 10/1985 | Johansson et al. . |
| 4,548,348 | 10/1985 | Clements . |
| 4,568,333 | 2/1986 | Sawyer et al. . |
| 4,627,844 | 12/1986 | Schmitt . |
| 4,636,412 | 1/1987 | Field . |
| 4,641,362 | 2/1987 | Muller . |
| 4,643,926 | 2/1987 | Mueller . |
| 4,650,452 | 3/1987 | Jensen . |
| 4,654,240 | 3/1987 | Johnston . |
| 4,680,208 | 7/1987 | Aoki et al. . |
| 4,683,916 | 8/1987 | Raines . |
| 4,684,364 | 8/1987 | Sawyer et al. . |
| 4,686,125 | 8/1987 | Johnston et al. . |
| 4,692,361 | 9/1987 | Johnston et al. . |
| 4,705,708 | 11/1987 | Briggs et al. . |
| 4,707,389 | 11/1987 | Ward . |
| 4,717,668 | 1/1988 | Keilman et al. . |
| 4,722,725 | 2/1988 | Sawyer et al. . |
| 4,724,961 | 2/1988 | Shimoyamada et al. . |
| 4,753,222 | 6/1988 | Morishita . |
| 4,764,404 | 8/1988 | Genske et al. . |
| 4,767,651 | 8/1988 | Starczewski et al. . |
| 4,772,497 | 9/1988 | Maasola . |
| 4,778,697 | 10/1988 | Genske et al. . |
| 4,800,129 | 1/1989 | Deak . |
| 4,803,102 | 2/1989 | Raniere et al. . |
| 4,829,002 | 5/1989 | Pattillo et al. . |
| 4,839,292 | 6/1989 | Cremonese . |
| 4,856,259 | 8/1989 | Woo et al. . |
| 4,856,260 | 8/1989 | Woo et al. . |
| 4,876,788 | 10/1989 | Steer et al. . |
| 4,885,119 | 12/1989 | Mueller et al. . |
| 4,910,085 | 3/1990 | Raniere et al. . |
| 4,910,147 | 3/1990 | Bacehowski et al. . |
| 4,923,470 | 5/1990 | Dumican . |
| 4,929,479 | 5/1990 | Shishido et al. . |
| 4,937,194 | 6/1990 | Pattillo et al. . |
| 4,939,151 | 7/1990 | Bacehowski et al. . |
| 4,948,643 | 8/1990 | Mueller . |
| 4,966,795 | 10/1990 | Genske et al. . |
| 4,968,624 | 11/1990 | Bacehowski et al. . |
| 4,978,579 | 12/1990 | Rosenbaum . |
| 5,006,114 | 4/1991 | Rogers et al. . |
| 5,066,290 | 11/1991 | Measells et al. . |
| 5,071,686 | 12/1991 | Genske et al. . |
| 5,085,649 | 2/1992 | Flynn . |
| 5,088,994 | 2/1992 | Porat et al. . |
| 5,093,164 | 3/1992 | Bauer et al. . |
| 5,098,202 | 3/1992 | Rosenbaum . |
| 5,108,844 | 4/1992 | Blemberg et al. . |
| 5,110,642 | 5/1992 | Genske . |
| 5,127,904 | 7/1992 | Loo et al. . |
| 5,129,894 | 7/1992 | Sommermeyer et al. . |
| 5,135,785 | 8/1992 | Millon . |
| 5,139,831 | 8/1992 | Mueller . |
| 5,139,946 | 8/1992 | Howell et al. . |
| 5,145,731 | 9/1992 | Lund et al. . |
| 5,176,634 | 1/1993 | Smith et al. . |
| 5,183,706 | 2/1993 | Bekele . |
| 5,185,189 | 2/1993 | Stenger et al. . |
| 5,225,346 | 7/1993 | Matsumiya et al. . |
| 5,226,564 | 7/1993 | Steer et al. . |
| 5,230,934 | 7/1993 | Sakano et al. . |
| 5,254,074 | 10/1993 | Landers et al. . |
| 5,272,084 | 12/1993 | O'Connell et al. . |
| 5,288,531 | 2/1994 | Falla et al. . |
| 5,298,300 | 3/1994 | Hosoi et al. . |
| 5,306,542 | 4/1994 | Bayer . |
| 5,310,676 | 5/1994 | Johansson et al. . |
| 5,334,180 | 8/1994 | Adolf et al. . |
| 5,348,525 | 9/1994 | Buchanan . |
| 5,348,794 | 9/1994 | Takahashi et al. . |
| 5,356,676 | 10/1994 | von Widdern et al. . |
| 5,356,709 | 10/1994 | Woo et al. . |
| 5,439,454 | 8/1995 | Lo et al. . |

FOREIGN PATENT DOCUMENTS

| | | |
|---|---|---|
| 0 589 575 A1 | 3/1994 | European Pat. Off. . |
| 2 587 935 | 4/1987 | France . |
| 14 11 850 | 10/1968 | Germany . |
| 34 14 199 | 10/1985 | Germany . |
| 623 736 | 5/1949 | United Kingdom . |
| 1 465 963 | 3/1977 | United Kingdom . |
| 2 177 974 | 2/1987 | United Kingdom . |
| WO 83/00158 | 1/1983 | WIPO . |
| WO 90/03427 | 4/1990 | WIPO . |
| WO 91/09719 | 7/1991 | WIPO . |
| WO 92/14600 | 9/1992 | WIPO . |
| WO 93/02859 | 2/1993 | WIPO . |
| WO 93/09718 | 5/1993 | WIPO . |
| WO 93/23093 | 11/1993 | WIPO . |
| WO 96/09233 | 3/1996 | WIPO . |

METHOD OF SEALING A PORT TUBE IN A CONTAINER

RELATED APPLICATIONS

This application is a continuation of U.S. patent application Ser. No. 08/675,529 filed Jul. 3,1996, now abandoned. U.S. patent application Ser. No. 08/675,529 is hereby incorporated herein by reference, and made a part hereof.

TECHNICAL FIELD

This invention relates generally to a port tube for use with containers and more specifically to a method for attaching a coextruded port tube to a medical grade container such as an I.V. bag.

BACKGROUND ART

In the medical delivery field, beneficial agents are packaged in flexible containers such as I.V. bags and are ultimately delivered through tubing such as an administration set to patients to achieve therapeutic effects. Port tubing is a necessary feature of the container and provides access to the contents of the container. I.V. bags are most commonly fabricated from polymers such as polyvinyl chloride, ethylene vinyl acetate, or polyolefin alloys, such as those disclosed in co-pending and commonly assigned U.S. patent Ser. No. 08/153,823. The I.V. containers usually have two confronting walls or panels that are attached to one another along a peripheral seam to make a fluid tight compartment.

Conventional containers employ port designs from one of two broad categories, panel ports and edge ports. Panel ports are attached to the container on a panel and are often centrally disposed. The panel port extends perpendicularly from the face of the panel. Edge ports are attached between the two panels along a peripheral seam of the container and extend parallel to the panels.

Panel ports are easily installed but have a number of drawbacks. First, panel ports, by design, necessitate the use of one or more injection molded parts. These injection molded parts are costly, especially at lower production volumes. Containers having panel ports also have the undesired tendency to retain a residual volume of fluid due to incomplete drainage.

Edge ports have a different set of design issues. Edge ports are prone to a defect known as "channel leak." Channel leak occurs along the port tube and results from an incomplete seal between the planar surfaces of the panels and the rounded surface of the port tube. Channel leak is more likely to occur when the container is fabricated from material that has a high modulus, and especially when using thin layers of such a stiff material, as the material will have a tendency to crease upon folding.

Prior attempts at overcoming the channel leak problems have led to the use of injection molded parts. These parts are commonly used in containers constructed from biaxially oriented nylon, foil, TEFLON®, polyester, and multilayer structures containing these polymers or inelastic materials. The injection molded parts are inserted between the panels and, in most instances, have a tapered outer profile. The purpose of the taper is to provide fillet material to the area where channel leak is likely to occur. Again, these injection molded parts are quite expensive, especially in low volume production.

U.S. Pat. No. 4,023,607 discloses a polyethylene urine bag having a polyethylene tubing inserted therein to provide access to the interior of the bag. The tubing is attached between two polyethylene film sheets that constitute the side walls of the bag. A heat sealing technique is used to seal the tube to the side walls. Shaped dies, as shown in FIG. 2 of the '607 Patent, are used in the heat sealing step. The tubing is "somewhat compressed" in the direction of the motion of the sealing dies during the heat sealing process. The '607 Patent does not fully compress the tubing to a flattened state and therefore requires attaching the container sidewalls to a rounded member. Such a procedure may lead to channel leak because it is difficult to form a good weld between planar members and rounded members.

The present invention is provided to solve these and other problems.

DISCLOSURE OF INVENTION

The present invention provides a method for connecting rounded members, such as port tubes, between planar members, such as the panels of I.V. bags. The method comprises several steps. The first step is providing a rounded member having a first or outer layer having a first melting temperature range, and a second or inner layer concentrically disposed within the outer layer and having a second melting temperature range, where the second melting temperature range is higher than the first melting temperature range. The second step is providing a pair of planar members having a melting temperature range within the first melting temperature range. In the third step, an end portion of the rounded member is positioned between perimeter edges of the pair of planar members to define an interface area. Pressure is applied to the interface area to collapse the end portion of the rounded member to essentially a flattened position. Sealing energies are applied, such as heat energy, to the interface area to heat the tubing to a temperature within the first melting temperature range but below the second melting temperature range, thereby forming a weld in the interface area. The pressure is released to the interface area wherein the end portion of the rounded member returns to a generally rounded position or some approximation thereof to an open position. In such a method, a seal can be formed without the use of a mandrel.

By collapsing the tubing at the time of sealing to the planar members, stress in the planar members is minimized because both the collapsed tubing and the planar members are flat or nearly flat when they are joined together. The incidence of channel leak is reduced because the planar members are sealed on a flat or nearly flat surface instead of having to form over a round surface.

Further, compressing the tubing to a flattened position provides the additional benefit of causing the sidewalls of the tubing to contact each other so that the die can compress the tubing and cause the first layer of the tubing to flow outward toward rounded end segments of the tubing to provide fillet material to the weld in the end segment area. The material of the first layer is essentially squeezed into the area where welding material is most needed. This helps reduce the incidence of channel leak.

Flattening the tubing during the sealing step also provides advantages during the manufacturing of containers over methods that seal over rounded tubing. In sealing planar sidewalls over a rounded tubing, a portion of the planar material in the side where the tubing is inserted conforms to the curved surface of the tubing. This causes a reduction in this side dimension in a linear direction in an amount proportionate to the diameter of the tubing. For containers that have a port tube only on one end of the container, the end of the container with the port tube will have a reduced linear dimension than the non-tubing end.

This discrepancy in dimensions on opposite ends of the planar members can cause ripples in the film in the side with the longer dimension an cause a crease in the seam which in turn can lead to channel leak. This discrepancy in dimensions may also lead to jamming of the container processing machinery or lead to other damage to the containers during processing. The dimensional differences in the planar material, which may be slight for a single container, can be multiplied in manufacturing processes that provide for forming multiple containers at a time from confronting webs of planar material.

Providing tubing material having multiple layers provides other benefits. For example, one can choose a material on the outside of the tubing that is compatible with the planar members and have an inner layer that is capable of being bonded to other materials using solvent bonding techniques. It is desirable to use polyolefins for tubing as they have many desirable characteristics. However, polyolefins, due to their inert nature, are typically not capable of being bonded using standard solvent bonding techniques. Materials such as PVC, on the other hand, bond well using solvent bonding techniques. Thus, in a multi-layered tubing it may be desirable to have an outer layer of a polyolefin that bonds well to the sheeting material and an inner layer material which is capable of solvent bonding to port closures, tubing harnesses, and other container access features.

The present invention also provides for sealing rounded members to planar members as described above but including the use of a mandrel. In this instance, there does not have to be a temperature difference between inner and outer tubing layers.

The present invention also provides for a tubing that has an outer layer capable of being thermal welded and an inner layer capable of being sealed using radio frequency energies. The inner and outer layers will have melting temperature differentials described above and be capable of being sealed inside a container using the above described process. Additional components may be attached to the port tube using RF sealing techniques.

The present invention further provides tubing having greater than two layers.

BEST MODE FOR CARRYING OUT THE INVENTION

Figure 1:
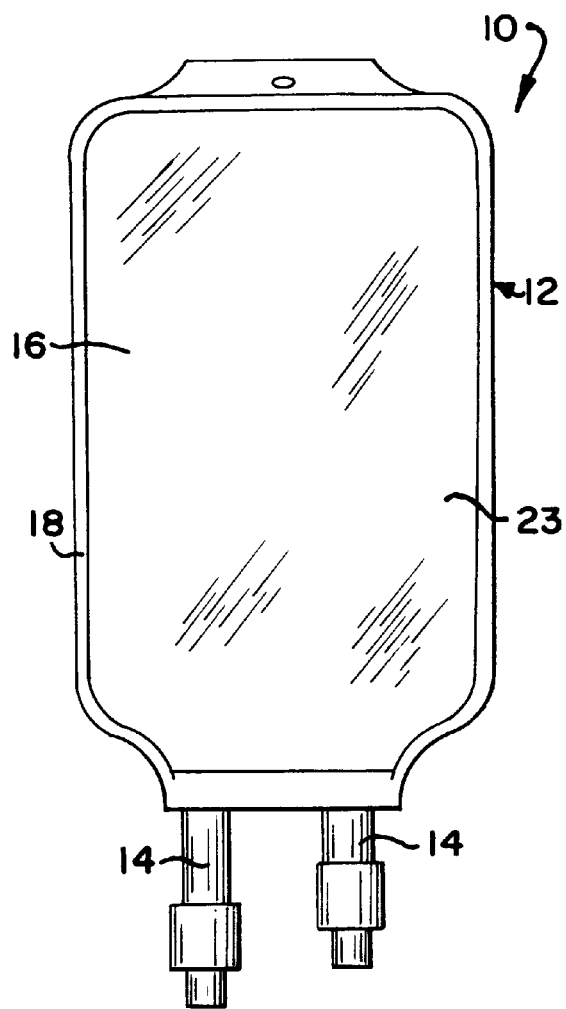
FIG. 1 is a front elevational view of a container having a pair of port tubes sealed in a perimeter edge of the container in accordance with the present invention.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring now to the drawings, FIG. 1 shows a container assembly, such as an I.V. bag, generally designated by the reference numeral 10. The assembly 10 includes a container 12 having port tubes 14 sealed in a perimeter edge of the container 12. The container 12 includes a pair of facing planar members 16, which are joined at their perimeter edges 18 and 22 (FIG. 4) to define a fluid compartment 23 therebetween. The planar members 16 can be constructed from a number of different materials including polyvinyl chloride, polyolefins, polyolefin copolymers, polyolefin alloys, and other materials as will be described in greater detail below.

Figure 2:
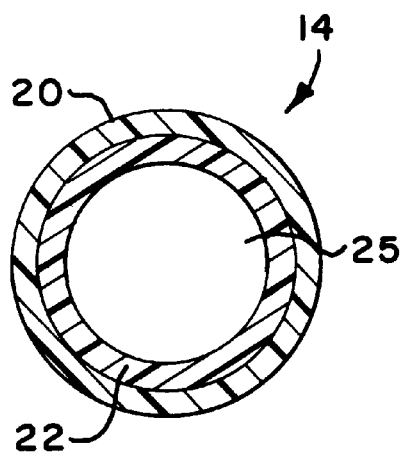
FIG. 2 is a schematic cross-sectional view of a two-layered coextruded tube made in accordance with the present invention.

FIG. 2 shows port tubing 14, including first or outer layer 20 and a second or inner layer 22 and a fluid passageway 25. The outer layer 20 has a first melting temperature range (T1) of about 60° C.–180° C., more preferably about 70° C.–125° C. and most preferably about 70° C.–100° C. and any combination or subcombination of ranges therein. The inner layer 22 has a second melting temperature range (T2) of about 70° C.–260° C., more preferably about 70° C.–150° C. and most preferably about 120° C.–125° C. and any combination or subcombination of ranges therein. The second melting temperature range T2 is preferably warmer than the first melting temperature where the difference between T2 and T1 is within a range of 1° C.–200° C. However, it is not necessary to have a temperature difference if using a mandrel.

As will be discussed in detail below, the port tubing 14 may be sealed to the planar members 16 using any energy source which causes melting of the sealing layers to form a weld between the port tubing 14 and the planar members 16. These energy sources include, but are not limited to, impulse welding techniques, constant temperature equipment, or induction welding techniques such as radio frequency. Any of these sealing energies whether causing heating through induction or conduction shall be collectively referred to as sealing energies.

The inner layer 22 should have a thickness within the range of 0.0001–0.010 inches, and the outer layer 20 should have a thickness within the range of 0.005–0.015 inches. The tubing 14 should have a combined wall thickness within the range of 0.005–0.025 inches.

Figure 9:
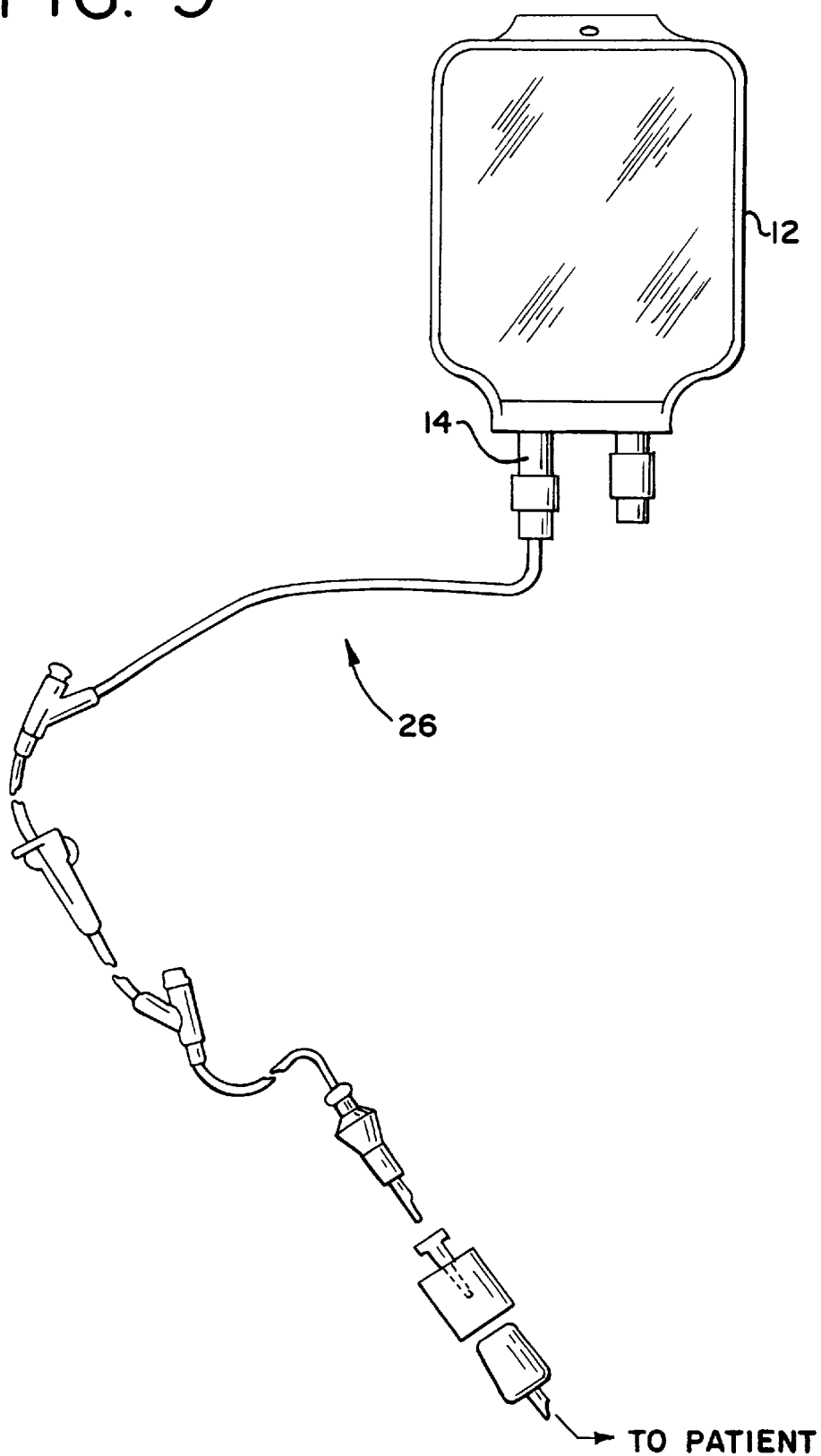
FIG. 9 is a schematic view of a fluid administration set.

Preferably for medical applications, the tubing wall thickness is negligible when compared to the inner diameter of the tubing. Thus, there is little difference between the inner and outer diameters of the tubing. For this reason, we shall generally refer to the tubing diameter without distinguishing between inner and outer tubing diameters. With this being stated, the port tubing 14 has a diameter from 0.10–1.0 inches. One of the advantages of the present invention is that a port tubing 14 may be sealed inside a container 12 without using a mandrel because the heat sealing process is controlled so that the outer layer 20 melts without melting the inner layer 22. Using a mandrel limits the length of a port tube as the mandrel must be inserted through a distal end of the tubing 14 into the fluid passageway 25 and into an area where the tubing 14 is sealed to the planar members 16. It is not practical to insert a mandrel through a long length of tubing. Thus, disposing of the need for a mandrel allows the port tubing 14 to be of a standard length of 0.375–1.0 inches as shown in FIG. 1, or extend from the container 12 to the patient and serve as a fluid administration set 26 as shown in FIG. 9.

The inner layer 22 should be composed of polyolefins, polyolefin copolymers, polyolefin alloys, polyamides, polyesters, and polyvinyl chloride (PVC) and block copolymers such as polyester-polyether block copolymers such as those sold under the trademark HYTREL®. Most preferably, the inner layer 22 is composed of polyvinyl chloride, as PVC is capable of being bonded using solvent bonding techniques. The PVC should have a melting temperature range of about 70° C.–140° C.

The outer layer 20 of the port tubing 14 is preferably composed of a polyolefin, polyolefin copolymers, or a polyolefin alloy. The polyolefin copolymers are from the reaction of an olefin monomer copolymerized with comonomers selected from aliphatic olefins, alpha-olefins, acrylic acid, methacrylic acid, ester derivatives of acrylic acid with alcohols having 1–10 carbons, ester derivatives of methacrylic acid with alcohols having 1–10 carbons, vinyl acetate, vinyl chloride and vinyl alcohol. More preferably the outer layer is an ethylene based copolymer consisting of ethylene copolymerized with a comonomer selected from the group of alpha-olefins, methyl acrylate, and vinyl acetate. Most preferably, the ethylene copolymer is a copolymer of about 85–95 mole percent ethylene and about 15 to about 5 mole percent butene-1. This copolymer will be referred to as an ultra-low density polyethylene (ULDPE) and is sold under the trade name TAFMERO®.

Suitable polyolefin alloys include those disclosed in commonly assigned U.S. patent Ser. No. 08153,823. For example, it may be desirable to use multiple component polymer alloys, such as a 3–5 component polymer alloys that are RF responsive or RF susceptible. What is meant by RF susceptible is that the material will have a dielectric loss when excited with a signal having a frequency between 1 and 60 MHz, and between the temperature range of 25–250° C., greater than or equal to 0.05 and more preferably greater than or equal to 0.1

In a first embodiment of an acceptable three component polymer alloy that is RF responsive, the first component will confer heat resistance and flexibility to the composition. This component may be selected from the group consisting of amorphous polyalpha olefins and preferably is a flexible polyolefin. These polyolefins should resist distortions to high temperatures up to 121° C., having a peak melting point of greater than 130° C. and be highly flexible, having a modulus of not more than 20,000 psi. Such a flexible polyolefin is sold under the product designation Rexene FPO 90007 which has a peak melting point of 145° C. and a modulus of 11,000 psi. In addition, certain polypropylenes with high syndiotacticity also posses the properties of high melting point and low modulus. The first component should constitute from 40–90% by weight of the composition.

The second component of the three component composition is an RF susceptible polymer which confers RF sealability to the composition and may be selected from either of two groups of polar polymers. The first group consists of ethylene copolymers having 50–85% ethylene content with at least one comonomer selected from the group consisting of acrylic acid, methacrylic acid, ester derivatives of acrylic acid with alcohols having 1–10 carbons, ester derivatives of methacrylic acid with alcohols having 1–10 carbons, vinyl acetate, and vinyl alcohol. The RF susceptible polymer may also be selected from a second group consisting of copolymers containing segments of polyurethane, polyester, polyurea, polyamide, polysulfones, and polyamides. These functionalities may constitute between 5–100% of the RF susceptible polymer. The RF susceptible polymer should constitute by weight from 5–50% of the composition. Preferably, the RF component is copolymers of ethylene methyl acrylate with methyl acrylate within the range of 15–25% by weight of the polymer.

The final component of the three component compound ensures compatibility between the first two components, and is selected from a styrene and hydrocarbon block copolymer and more preferably a styrene-ethylene-butene styrene block (SEBS) copolymer, styrenic block copolymers and most preferably SEBS block copolymer that is maleic anhydride functionalized. The third component should constitute by weight within the range of 5–30% of the composition.

In a second embodiment of the three component polymer alloy, the first component confers RF sealability and flexibility over the desired temperature range. The first component confers high temperature resistance ("temperature resistant polymer") and is chosen from the group consisting of polyamides, polyimides, polyurethanes, polypropylene and polymethylpentene. Preferably the first component constitutes by weight within the range of 30–60% of the composition, and preferably is polypropylene. The second component confers RF sealability and flexibility over the desired temperature range. The RF polymer is selected from the first and second groups identified above with the exception of ethylene vinyl alcohol. The second component should constitute by weight within the range of 30–60% of the composition. The third component ensures compatibility between the first two components and is chosen from SEBS block copolymers and preferably is maleic anhydride functionalized. The third component should constitute within the range of 5–30% by weight of the composition.

As for four and five component polymer alloys that are RF responsive, the first component confers heat resistance. This component may be chosen from polyolefins, most preferably polypropylenes, and more specifically the propylene alpha-olefin random copolymers (PPE). Preferably, the PPE's will have a narrow molecular weight range. However, by themselves, the PPE's are too rigid to meet the flexibility requirements. When combined by alloying with certain low modulus polymers, good flexibility can be achieved. Examples of acceptable PPE's include those sold under the product designations Soltex 4208, and Exxon Escorene PD9272.

These low modulus copolymers can include ethylene based copolymers such as ethylene-co-vinyl acetate ("EVA"), ethylene co-alpha olefins, or the so-called ultra low density (typically less than 0.90 Kg/L) polyethylenes ("ULDPE"). These ULDPE include those commercially available products sold under the trademarks TAFMER® (Mitsui Petrochemical Co.) under the product designation A485, EXACT® (Exxon Chemical Company) under the product designations 4023–4024, and INSITE® technology polymers (Dow Chemical Co.). In addition, poly butene-1 ("PB"), such as those sold by Shell Chemical Company under product designations PB-8010, PB-8310; thermoplastic elastomers based on SEBS block copolymers, (Shell Chemical Company), poly isobutene ("PIB") under the product designations Vistanex L-80, L-100, L-120, L-140 (Exxon Chemical Company), ethylene alkyl acrylate, the methyl acrylate copolymers ("EMA") such as those under the product designation EMAC 2707, and DS-1130 (Chevron), and n-butyl acrylates ("ENBA") (Quantum Chemical) were found to be acceptable copolymers. Ethylene copolymers such as the acrylic and methacrylic acid copolymers and their partially neutralized salts and ionomers, such as PRIMACORO (Dow Chemical Company) and SURYLN® (E.I. DuPont de Nemours & Company) were also satisfactory.

Preferably the first component is chosen from the group of polypropylene homo and random copolymers with alpha olefins which constitute by weight approximately 30–60%, more preferably 35–45%, and most preferably 45%, of the composition and any combination or subcombination of ranges therein. For example, random copolymers of propylene with ethylene where the ethylene content is in an amount within the range of 1–6%, and more preferably 2–4%, of the weight of the polymer is preferred as the first component.

The second component of the four component polymer alloy confers flexibility and low temperature ductility and is a second polyolefin different than that of the first component wherein it contains no propylene repeating units ("non propylene based polyolefin"). Preferably it is ethylene copolymers including ULDPE, polybutene, butene ethylene copolymers, ethylene vinyl acetate, copolymers with vinyl acetate contents between approximately 18–50%, ethylene methyl acrylate copolymers with methyl acrylate contents being between approximately 20–40%, ethylene n-butyl acrylate copolymers with n-butyl acrylate content of between 20–40%, ethylene acrylic acid copolymers with the acrylic acid content of greater than approximately 15%. An example of these products are sold under such product designations as TAFMER® A-4085 (Mitsui), EMAC DS-1130 (Chevron), Exact 4023, 4024 and 4028 (Exxon). More preferably, the second component is either ULDPE sold by Mitsui Petrochemical Company under the designation TAFMER A-4085, or polybutene-1, PB8010 and PB8310 (Shell Chemical Co.), and should constitute by weight approximately 25–50%, more preferably 35–45%, and most preferably 45%, of the composition and any combination or subcombination of ranges therein.

To impart RF dielectric loss to the four component composition, certain known high dielectric loss ingredients ("RF susceptible polymers") are included in the composition. These polymers may be selected from the group of RF polymers in the first and second group set forth above.

Other RF active materials include PVC, vinylidine chlorides, and fluorides, copolymer of bis-phenol-A and epichlorohydrines known as PHENOXYS® (Union Carbide). However, significant contents of these chlorine and fluorine containing polymers would render the composition environmentally unsound as incineration of such a material would generate inorganic acids.

The polyamides of the RF susceptible polymer are preferably selected from aliphatic polyamides resulting from the condensation reaction of di-amines having a carbon number within a range of 2–13, aliphatic polyamides resulting from a condensation reaction of di-acids having a carbon number within a range of 2–13, polyamides resulting from the condensation reaction of dimer fatty acids, and amides containing copolymers (random, block, and graft). Polyamides rarely are found in the layer which contacts medical solutions as they typically contaminate the solution by leaching out into the solution. However, it has been found by the Applicants of the present invention that the most preferred RF susceptible polymer are a variety of dimer fatty acid polyamides sold by Henkel Corporation under the product designations MACROMELT and VERSAMID, which do not lead to such contamination. The RF susceptible polymer preferably should constitute by weight approximately 5–30%, more preferably between 7–13%, and most preferably 10%, of the composition and any combination or subcombination of ranges therein.

The fourth component of the composition confers compatibility between the polar and nonpolar components of the composition (sometimes referred to as a "compatibilizing polymer") and preferably is styrenic block copolymers with hydrocarbon soft segments. More preferably, the fourth component is selected from SEBS block copolymers that are modified by maleic anhydride, epoxy, or carboxylate functionalities, and preferably is an SEBS block copolymer that contains maleic anhydride functional groups ("functionalized"). Such a product is sold by Shell Chemical Company under the designation KRATON® RP-6509. The compatibilizing polymer should constitute by weight approximately 5–40%, more preferably 7–13%, and most preferably 10% of the composition and any combination or subcombination of ranges therein.

It may also desirable to add a fifth component of a nonfunctionalized SEBS block copolymer such as the ones sold by Shell Chemical Company under the product designations KRATON G-1652 and G-1657. The fifth component should constitute by weight approximately 5–40%, and more preferably 7–13% and any combination or subcombination of ranges therein.

Another acceptable polymer alloy is a blend of styrene-ethylene-butene-styrene ("SEBS") block copolymer (40%–85% by weight), ethylene vinyl acetate (0–40% by weight), and polypropylene (10%–40% by weight)

The planar members 16 may be composed of PVC, polyolefins, polyolefin copolymers (as described above), polyolefin alloys (as described above), polyesters, and polyamides. Most preferably, the planar members 16 are composed of a polymeric material compatible with the first layer 20 and more preferably a polyolefin or PVC.

Preferably, the tubing 14 is constructed by coextruding the first and second layers 20 and 22 through a conventional coextruder die to produce a tubing 14 having two distinct layers. Other manufacturing methods can also be used to produce a tube useful with the present invention although coextrusion is preferred.

Figure 2A:
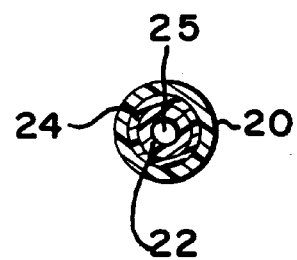
FIG. 2a is a cross-sectional view of a three-layered coextruded tube made in accordance with the present invention

The port tubing 14 could also include additional layers, if desired. For example, it may be desirable to have a tie layer 24 between the inner 22 and outer layers 20. (FIG. 2a) The tie layer 24 may be selected from modified polyolefins, and modified ethylene and propylene copolymers, such as those sold under the product designations Admer (Mitsui), which is a maleic anhyrdride modified polypropylene, Prexar (Quantum Chemical Co.) and Bynel (Dupont). The tie layer 24 should be as thin as practical and have a thickness from 0.0003 inches to 0.0007 inches. If additional layers are used, it remains important that the melting temperature range T2 of the inner layer 22 be higher than the melting temperature range T1 of the outer layer 20.

Although a circular-shaped port tubing 14 is shown in FIG. 2, other tubing could be used having other cross-sectional shapes, including oval or polygonal cross-sections.

To seal a rounded member such as the port tubing 14 between the planar members 16 of the container 12, the port tubing 14 is collapsed to a flattened position using a die while applying sealing energies through the die. The sealing process may be carried out using flat or shaped welding dies. The dies are typical of those found in industry. The process will first be described using flat welding dies (FIG. 4) and then will be described using shaped welding dies (FIGS. 5–8).

Figure 4:
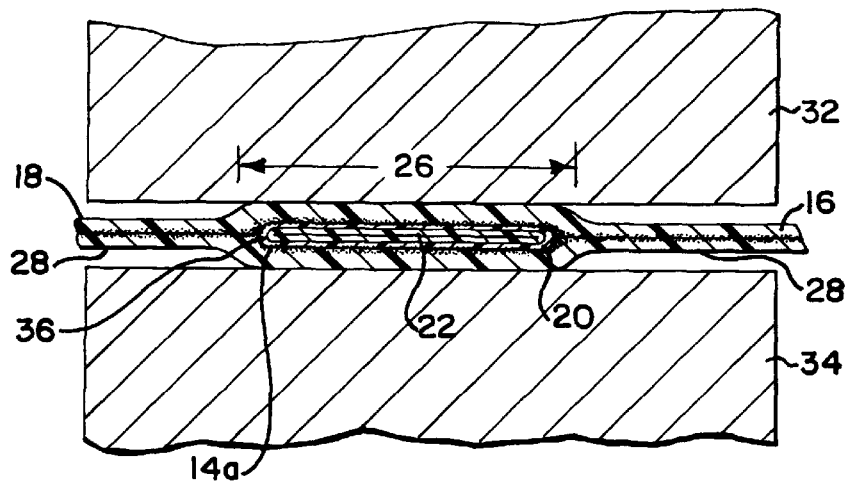
FIG. 4 is a cross-sectional view showing the port tube in a perimeter edge of the container between flat welding dies.

FIG. 4 shows a pair of conventional flat, mating welding dies 32, 34 used in the heat sealing process. An end portion 14a of the port tubing 14 is positioned between the perimeter edges 18 of the pair of planar members 16 to define an interface area 26. The interface area 26, as indicated by the arrows, includes the area where the planar members 16 bond to the tubing 14. A portion 28 of each of the planar members 16 extends outward from the interface area 26. It is of couse possible to apply sealing energies through a single die without departing from the spirit of the invention.

If desired, a flat shim, or mandrel can be inserted into the fluid passageway 25 of the tubing 14 in the interface area 26 to assure that the inner layer 22 of the tubing 14 will not be welded to itself during the sealing process and to allow for positioning of the tubing 14 in a desired orientation. The use of the mandrel is optional as its use may be avoided by carefully controlling the energy or heat applied in the process of the present invention. However, by using a mandrel there is no need to have a temperature difference between the inner and outer tubing layers 20, 22.

As further shown in FIG. 4, the interface area 26 is then positioned between the pair of flat welding dies 32, 34. The welding dies 32, 34 are closed to apply pressure to the interface area 26. The welding dies 32, 34 also apply sealing energies, such as heat, within the melting temperature range T1. When the tubing 14 is collapsed to a flattened state, the compression of the die 32, 34 will cause the material of the outer layer 20 to flow toward rounded end members 36 of the tubing 14 to supply additional material or fillet material to a weld. This will improve the weld between the rounded members 36 and the perimeter edges 18 and further reduce the likelihood of channel leak.

FIG. 4 shows the end portion 14a collapsed to essentially a completely flattened position where the inner layer 22 of the port tubing 14 contacts itself. Sealing energy is applied through the welding dies 32, 34 to the interface area 26 to reach a temperature in the port tubing 14 within the first melting temperature range T1 but below the second melting temperature range T2. The weld between the tubing 14 and the perimeter edges 18 is thereby formed in the interface area 26.

Specifically, the outer layer 20 of the port tubing 14 and perimeter edges 18 of the planar members 16 soften and melt together at the interface area 26. Thus, the planar members 16 are welded around an entire periphery of the end portion 14a of the port tubing 14. Compressive forces are continually applied until the dies contact the planar members which linearly extend beyond the interface area 26, and are welded to each other as well.

After the sealing process is complete, the welding dies 32, 34 are opened, thereby releasing the pressure to the interface area 26. Because the sealing energy is applied at a temperature less than the melting temperature range T2 of the inner layer 22, the inner layer 22 does not melt and is not welded to itself. Therefore, the collapsed end portion 14a of the port tubing 14 then returns to a rounded or open position to provide a pathway for the contents stored in the container.

An improved weld is provided by collapsing the port tubing 14 between the planar members 16 at the time of sealing. Stress in the planar members 16 adjacent to the weld is minimized because both the collapsed port tubing 14 and planar members 16 are flattened when joined together. When sealing in this flattened position, pressure is applied normal to the planar members 16 improving the adhesion between the outer layer 20 and the planar members 16 at the interface area 26. Also, the planar members 16 are not required to be stretched about the outer circumference of a rigid port tubing 14. Consequently, stress is minimized in the planar members 16 adjacent to the weld, significantly reducing the tendency of the planar members 16 to separate from the port tubing 14 and cause channel leak. Further, as discussed above, there is minimal reduction in the dimension of the planar members 16 to help avoid processing difficulties.

In a further attribute of the process, as sealing energy is continually applied to the interface area 26 and pressure is applied to the flattened tubing 14, the outer layer 20 of the port tubing 14 continues to melt, allowing a portion of the outer layer 20 to flow and provide fillet material to the weld in the interface area 26. This further improves the seal between the outer layer 20 and the planar members 16 because material can flow to fill any voids or gaps present between the outer layer 20 and planar members 16.

Figure 5:
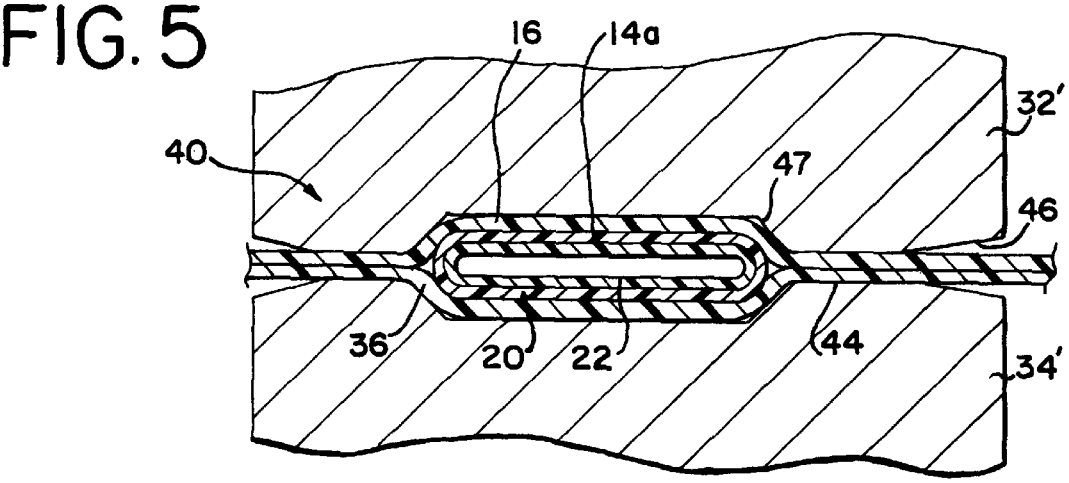
FIG. 5 is a cross-sectional view showing the port tube in the container between a first set of shaped welding dies, where the dies are partially open.
Figure 6:
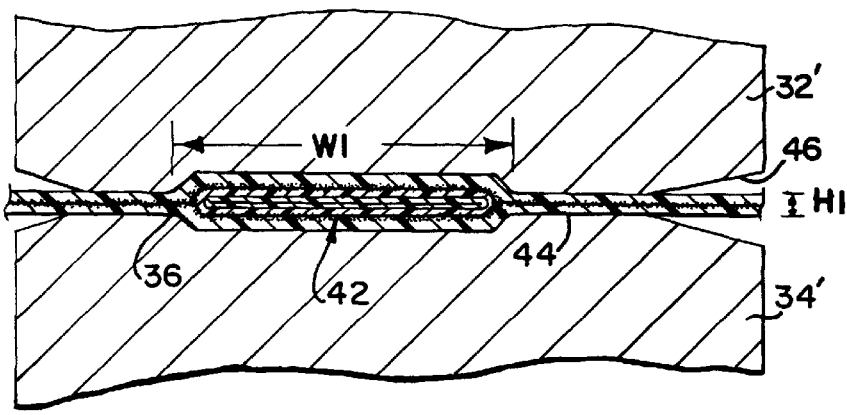
FIG. 6 is a cross-sectional view showing the port tube and container of FIG. 5 where the dies are closed.
Figure 7:
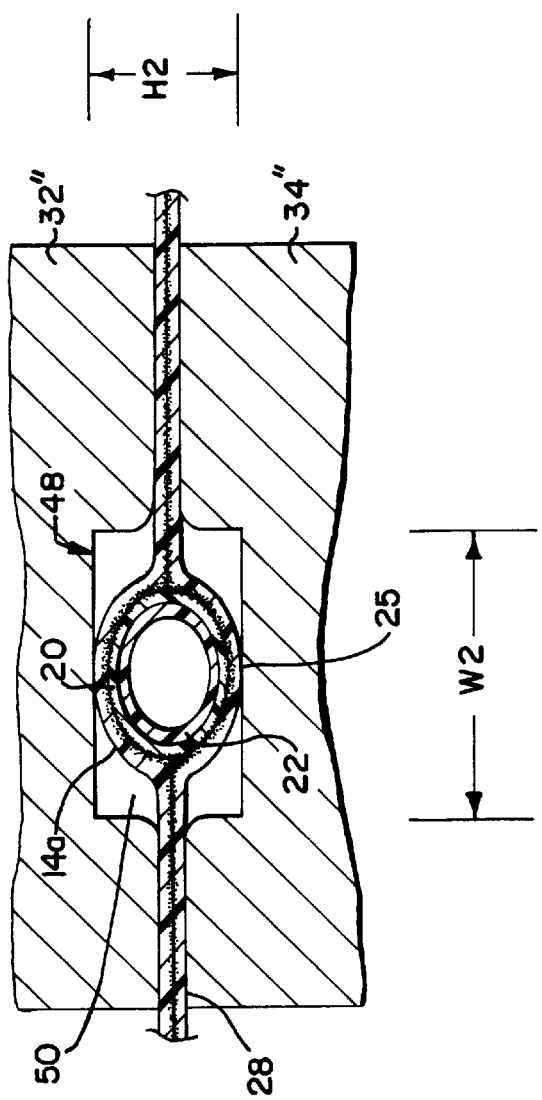
FIG. 7 is a cross-sectional view showing the port tube and container of FIGS. 5 and 6 between a second set of shaped dies where the dies are closed.

FIGS. 5–7 illustrate the process of the present invention using shaped welding dies 32', 34'. Generally, two different pairs of shaped welding dies are utilized. It may be desirable to use shaped welding dies 32', 34' when there is a small difference in the melting temperature ranges T1 and T2 such as less than 20°C. In such cases, there is a greater risk of inadvertently melting the inner layer 22 to itself during the sealing process.

Figure 3:
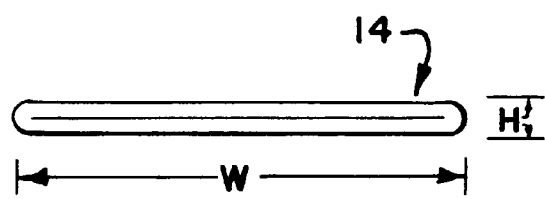
FIG. 3 is an end view of a port tube collapsed to a flattened position.

As shown in FIG. 5, each of the first pair of shaped dies 32', 34' has a trapezoidal-shaped portion 40. FIG. 5 shows the dies 32', 34' in a partially open condition. When the dies are closed (FIG. 6), the trapezoidal portions 40 confront each other in mirrored relation to form a first mold 42 that is dimensioned to accommodate the interface area 26 when the end portion 14a of the port tubing 14 is collapsed to a flattened position between the planar members 16. The first mold 42 has a height H1 and width W1 each respectively less than a height H and width W of the port tubing 14 when in a unconstrained flattened position as shown in FIG. 3. As further shown in FIGS. 5–6, each of the first set of dies 32', 34' also has flat portions 44 extending on each side of the first mold 42 and additional inclined sections 46 extending from the flat portions 44 of the dies 32', 34'.

As shown in FIG. 7, each of the second pair of shaped dies 32", 34" has a rectangular-shaped portion 48. When the dies 32", 34" are closed, the rectangular portions 48 confront each other to form a second mold 50. The second mold 50 is dimensioned to accommodate the interface area 26 when the end portion 14a of the port tubing 14 has returned to a rounded position. The second mold 50 has a height H2 greater than H1 but a width W2 that is less than W1. Thus, the interface area 26 is not compressed in the second mold 50.

To seal the port tubing 14 in the container 12, the end portion 14a of the port tubing 14 is positioned between the planar members 16 of the container 12 to define the interface area 26. As shown in FIG. 5, the interface area 26 is then positioned between the first pair of dies 32', 34' in the first mold 42. FIG. 5 shows the dies 32', 34' in a partially opened position.

FIG. 6 shows the dies 32', 34' fully closed, collapsing the port tube end 14a to essentially a completely flattened position. Because the height H1 and width W1 of the first mold 42 are less than the height H and width W of the flattened port tubing 14 in an unconstrained position, the planar members 16 and port tube end portion 14a are compressed about a total periphery of the interface area 26 when the dies 32', 34' close. Sealing energy is applied through the dies, thereby forming a weld in the interface area 26. The planar members 16 are welded around an entire periphery of the port tube end portion 14a. The flat portions 44 of the first set of dies 32', 34' seal portions 28 of the planar members 16 to seal the container 12. It is also possible to apply sealing energy followed by collapsing the interface area 26.

When the port tubing 14 is collapsed, the port tubing 14 has curved end members 36 (FIG. 5). Channel leak is most likely to occur in the area of the curved end members 36 because a weld must be formed between the planar member 16 to a curved segment. Inclined surfaces 46 of the dies 32', 34' are provided to apply pressure and sealing energies to the curved end members 36 to improve the seal between the port tubing 14 and planar members 16.

Once sealed, the first set of shaped dies 32', 34' are opened to release the pressure on the interface area 26. The end portion 14a of the port tubing 14 then returns to a rounded or open position. The tubing 14 and planar members 16 are removed from between the dies 32', 34' and then, as shown in FIG. 7, are positioned between the second pair of shaped dies 32", 34".

The second set of dies 32", 34" seal an end of the container 12 to form a bottom wall of the container 12. When the dies 32", 34" are closed, the second mold 50 accommodates the rounded shape of the port tubing 14. Sealing energies are applied through the second pair of dies 32", 34" to seal together, a second time, the portion 28 of the planar members 16. Because the width W2 of the second mold 50 is less than the width W1 of the first mold 42, portions of the planar members 16 closest to the interface area 26 are sealed again, further assuring no channel leaks will be present around the port tubing 14. Once the second pair of dies 32", 34" has sealed the planar members 16 a second time, the interface area 26 is removed from the dies 32", 34" and the sealing process is complete.

Figure 8:
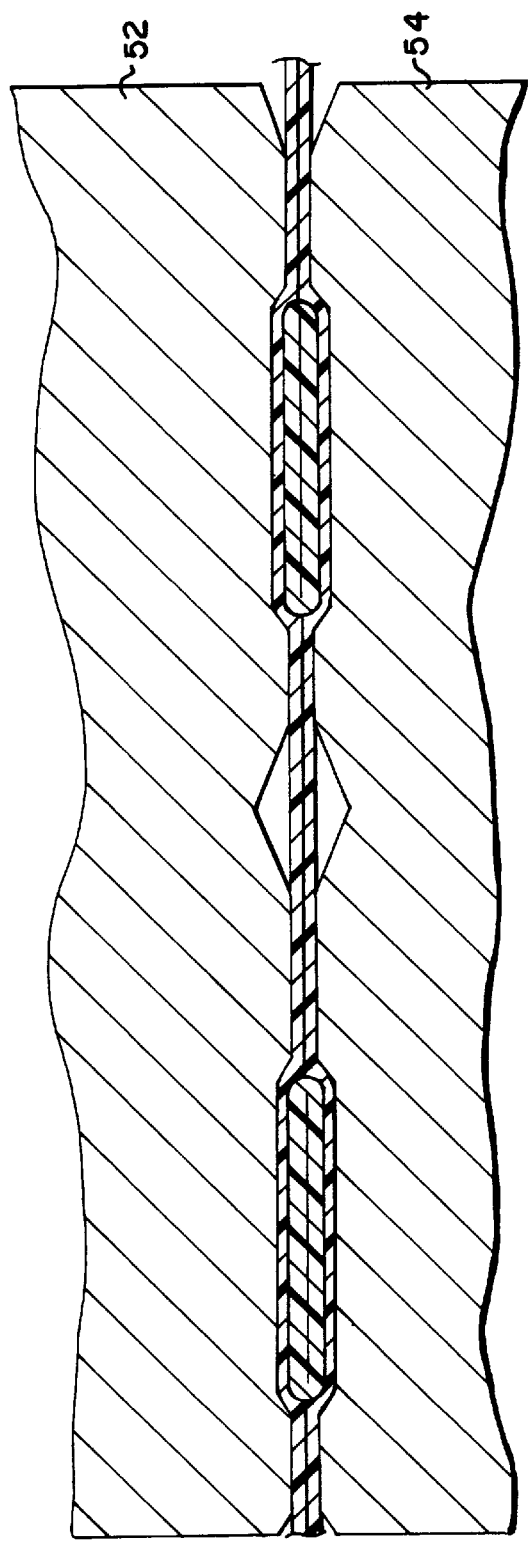
FIG. 8 is a cross-sectional view showing a pair of port tubes being sealed simultaneously in a perimeter edge of a container.

FIG. 8 shows an additional set of shaped dies 52, 54 similar to the dies 32', 34' in FIG. 6 which are adapted to simultaneously seal two port tubes 14 in a container according to the process of the present invention.

It should be understood that it is possible to apply sealing energy to a die prior to collapsing the port tube 14 or afterward depending on the welding techniques being used.

By way of example, and not limitation, examples of the present invention will now be given illustrating the port tubes being sealed between planar members to form fluid containers. The materials in each of these containers are shown in the Table below.

The tubing components were tumble blended and formed into tubing, with the exception of Example 2, in a 1¼ inch Davis Standard Extruder and a Genca cross-head die. The tubing had an inner diameter of 0.103 inches and an outer diameter of 0.140 inches. The tubing components of Example 2 were made into tubing in a larger diameter extruder and die head to form tubing having an outer diameter of 0.4 inches.

Each of the tubings were heat sealed between planar members, of the material set forth in the Table below, using a set of flat dies to form a fluid container.

The containers were inflated with air and found to be air tight. Therefore, the containers did not experience channel leak. Further, the container of Example 6 was filled with water and centrifuged at 1,800 xg for three hours without leakage or seal failure.

| EXAMP. NUMBER | 1ST TUBING LAYER | 2ND TUBING LAYER (TIE) | 3RD TUBING LAYER | PLANAR MEMBERS |
|---|---|---|---|---|
| 1 | ULDPE | NONE | PVC | LDPE\POLYESTER |
| 2 | ULDPE | ADMER | PVC | LDPE\POLYESTER |
| 3 | ULDPE | ADMER | POLYAMIDE | POLYOLEFIN ALLOY I[1] |
| 4 | ULDPE | ADMER | POLYPROPYLENE | POLYOLEFIN ALLOY I[1] |
| 5 | POLYOLEFIN ALLOY II[2] | ADMER | PVC | POLYOLEFIN ALLOY II[2] |
| 6 | POLYOLEFIN ALLOY II[2] | ADMER | PVC | POLYOLEFIN ALLOY II[2]/POLYSTYRENE |

[1]Polyolefin alloy of polypropylene/ULDPE/dimer fatty acid polyamide/SEBS
[2]Polymer blend of styrene-ethylene-butene-styrene ("SEBS") block copolymer (40%–85% by weight), ethylene vinyl acetate (0–40% by weight), and polypropylene (10%–40% by weight)

While specific embodiments have been illustrated and described, numerous modifications are possible without departing from the spirit of the invention, and the scope of protection is only limited by the scope of the accompanying Claims.

We claim:

1. A method for connecting rounded members between planar members comprising the steps of:

providing a rounded member having an outer layer having a first melting temperature range and an inner layer concentrically disposed within the outer layer and having a second melting temperature range, the second melting temperature range being warmer than the first melting temperature range;

providing a pair of opposed planar members, the planar members each having a melting temperature within the first melting temperature range;

positioning an end portion of the rounded member between perimeter edges of the pair of planar members to define an interface area;

applying pressure to the interface area to collapse the end portion of the rounded member to essentially a flattened position;

applying sealing energy to the interface area to heat the rounded member to a temperature within the first melting temperature range but below the second melting temperature range, thereby forming a weld between the planar members, and the rounded member in the interface area; and, releasing the pressure to the interface area wherein the end portion of the rounded member returns to an open position.

2. The method of claim 1 including the step of flowing a portion of the first layer of the rounded member to provide fillet material in a portion of the interface area.

3. The method of claim 1 wherein the collapsed rounded member has curved end segments and including the steps of applying pressure and sealing energy to the curved end segments.

4. The method of claim 1 wherein a portion of the perimeter edges of the planar members extend beyond the interface area, the method further including the steps of applying pressure and sealing energy to the perimeter edges beyond the interface area to seal the planar members together.

5. The method of claim 4 wherein the steps of applying pressure and sealing energy to the perimeter edges beyond the interface area are done simultaneously with the step of forming a weld in the interface area.

6. The method of claim 4 wherein the steps of applying pressure and sealing energy to the perimeter edges beyond the interface area are carried out after the step of forming a weld in the interface area.

7. The method of claim 1 wherein the steps of applying sealing energy and pressure to the tubing in the interface area comprises the steps of:

providing a welding die;

supplying heating energy through the die; and closing the welding die.

8. The method of claim 7 wherein the step of applying heating energy through the die is done before the step of closing the welding die.

9. The method of claim 7 wherein the step of applying heating energy through the die is done after the step of closing the die.

10. The method of claim 7 wherein the welding die is a flat welding die.

11. The method of claim 7 wherein the welding die is a shaped welding die.

12. The method of claim 11 wherein a portion of the perimeter edges of the planar members extend beyond the interface area, the method further comprising the steps of:

providing a second shaped welding die being movable between an opened position and a closed position, the second welding die defining a mold while in the closed position, the mold being dimensioned to accommodate the tubing without compressing the tubing; and closing the second welding die to seal the perimeter edges extending beyond the interface area.

13. A method of connecting a medical tubing to a medical container, the tubing having an outer layer with a first melting temperature range and an inner layer concentrically disposed within the outer layer and having a second melting temperature range, the second melting temperature range being warmer than the first melting temperature range, the container having opposed walls with perimeter edges and the walls having a melting temperature range within the first melting temperature range, the method comprising the steps of:

positioning an end portion of the tube between the perimeter edges of the opposed walls to define an interface area;

providing a welding apparatus having a die;

placing the interface area in the welding apparatus;

activating the die to collapse the end portion of the tube between the perimeter edges; and, applying sealing energy through the die at a temperature within the first melting temperature range but less than the second melting temperature range forming a weld in the interface area.

14. The method of claim 13 wherein the welding die is a flat welding die.

15. The method of claim 13 wherein the welding die is a shaped welding die.

16. The method of claim 13 wherein the step of applying sealing energy includes flowing a portion of the outer layer of the end portion of the tubing to provide fillet material to the weld.

17. The method of claim 13 wherein the collapsed tubing has curved end segments and the method including the steps of applying pressure and sealing energy to the curved end segments.

18. The method of claim 13 wherein a portion of the perimeter edges of the planar members extend beyond the interface area, the method further including the steps of applying pressure and sealing energy to the perimeter edges beyond the interface area.

19. The method of claim 18 wherein the steps of applying pressure and sealing energy to the perimeter edges beyond the interface area is carried out simultaneously with the step of forming a weld in the interface area.

20. The method of claim 18 wherein the steps of applying pressure and sealing energy to the perimeter edges beyond the interface area is carried out after the step of welding the interface area.

21. The method of claim 13 wherein the step of activating the die to collapse the end portion of the tube between the perimeter edges is done before the step of applying sealing energy through the die.

22. The method of claim 13 wherein the step of activating the die to collapse the end portion of the tube between the perimeter edges is done after the step of applying sealing energy through the die.

* * * * *